(12) United States Patent
Lu et al.

(10) Patent No.: US 10,786,507 B2
(45) Date of Patent: Sep. 29, 2020

(54) PHARMACEUTICAL COMPOSITION CONTAINING JAK KINASE INHIBITOR OR PHARMACEUTICALLY ACCEPTABLE SALT THEREOF

(71) Applicant: Jiangsu Hengrui Medicine Co., Ltd., Lianyungang, Jiangsu (CN)

(72) Inventors: Yun Lu, Jiangsu (CN); Hao Chen, Jiangsu (CN); Xiaochen Pan, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/077,135

(22) PCT Filed: Feb. 17, 2017

(86) PCT No.: PCT/CN2017/073869
§ 371 (c)(1),
(2) Date: Aug. 10, 2018

(87) PCT Pub. No.: WO2017/140254
PCT Pub. Date: Aug. 24, 2017

(65) Prior Publication Data
US 2019/0030033 A1   Jan. 31, 2019

(30) Foreign Application Priority Data

Feb. 19, 2016 (CN) .......................... 2016 1 0094168

(51) Int. Cl.
*A61K 31/519* (2006.01)
*A61K 9/20* (2006.01)

(52) U.S. Cl.
CPC .......... *A61K 31/519* (2013.01); *A61K 9/2018* (2013.01); *A61K 9/2054* (2013.01); *A61K 9/2027* (2013.01); *A61K 9/2059* (2013.01)

(58) Field of Classification Search
CPC .................................................. C07D 473/34
See application file for complete search history.

(56) References Cited

U.S. PATENT DOCUMENTS

| 9,527,851 B2* | 12/2016 | Zhang | A61K 45/06 |
| 2014/0234417 A1* | 8/2014 | Inoue | A61K 31/496 |
| | | | 424/474 |
| 2014/0336207 A1* | 11/2014 | Zhang | A61K 45/06 |
| | | | 514/265.1 |
| 2018/0237438 A1* | 8/2018 | Sun | A61K 31/519 |

FOREIGN PATENT DOCUMENTS

| CN | 104470927 A | 3/2015 |
| CN | 103415520 B | 1/2016 |
| WO | 2013091539 A1 | 6/2013 |
| WO | 2014194741 A1 | 12/2014 |
| WO | 2016054959 A1 | 4/2016 |
| WO | 2016070697 A1 | 5/2016 |

OTHER PUBLICATIONS

T. Kupiec, International Journal of Pharmaceutical Compounding (2004) (Year: 2004).*
L.P. Landim et al., Rev. Bras. Farmacogn. Braz. J. Pharmacogn (2013) (Year: 2013).*
The second method (paddle method) of the dissolution rate test described in the appendix of vol. II of Chinese Pharmacopoeia 2010 Edition.
Int'l Search Report dated May 24, 2017 in Int'l Application No. PCT/CN2017/073869.

* cited by examiner

Primary Examiner — Mark L Shibuya
Assistant Examiner — Ebenezer O Sackey
(74) Attorney, Agent, or Firm — Ice Miller LLP

(57) ABSTRACT

Provided in the present invention is a pharmaceutical composition containing a JAK kinase inhibitor or a pharmaceutically acceptable salt thereof. In particular, provided in the present invention is a pharmaceutical composition containing (3aR, 5s, 6aS)-N-(3-methoxy-1,2,4-thiadiazol-5-yl)-5-(methyl(7H-pyrrolo [2,3-d] pyrimidin-4-yl) amino) hexahydrocyclopenta [c] pyrrol-2 (1H)-carboxamide, or a pharmaceutically acceptable salt thereof, and cellulose ether. The pharmaceutical composition of the present invention is characterized by a rapid dissolution rate and good stability.

12 Claims, 2 Drawing Sheets

PHARMACEUTICAL COMPOSITION CONTAINING JAK KINASE INHIBITOR OR PHARMACEUTICALLY ACCEPTABLE SALT THEREOF

CROSS-REFERENCE TO RELATED APPLICATION

This application is a Section 371 of International Application No. PCT/CN2017/073869, filed Feb. 17, 2017, which was published in the Chinese language on Aug. 24, 2017, under International Publication No. WO 2017/140254 A1, which claims priority under 35 U.S.C. § 119(b) to Chinese Application No. 201610094168.2, filed Feb. 19, 2016, the disclosures of which are incorporated herein by reference in their entirety.

FIELD OF THE INVENTION

The present invention belongs to the field of pharmaceutical formulations. Specifically, the present invention relates to a pharmaceutical composition comprising a JAK kinase inhibitor or a pharmaceutically acceptable salt thereof.

BACKGROUND OF THE INVENTION

Arthritis is the most common chronic disease in the world. There are about 355 million patients suffering from arthritis in the world, and more than 100 million patients are in China. The best-selling drugs currently used for the treatment of rheumatoid arthritis in the pharmaceutical market are mostly injectable drugs. Although the commonly used oral drug methotrexate has a significant efficacy, it has a high toxicity. Tofacitinib (tasocitinib, CP-690550), developed by Pfizer, is a Janus kinase (JAK) inhibitor. Clinical trial results show that Pfizer's tofacitinib has a significantly better efficacy than that of methotrexate, and can effectively improve various syndromes in patients with rheumatoid arthritis. Based on the structure of tofacitinib, a series of JAK kinase inhibitors, which are active in vitro and in vivo and highly absorbable, have been developed. WO2013091539 discloses a series of novel JAK kinase inhibitors, including the compound of formula A as shown below, with a chemical name of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide. WO2014194741 further discloses a bisulfate of the compound. WO2016054959 and WO2016070697 disclose the crystal forms I and II of the bisulfate of the compound, respectively.

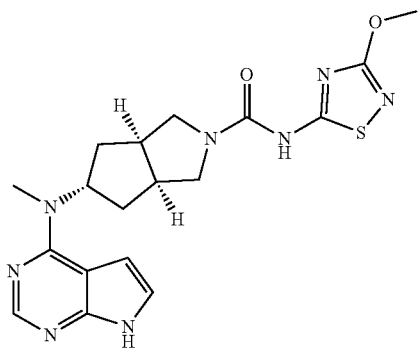

A

However, none of these documents disclose how to formulate compound A or a pharmaceutically acceptable salt thereof into a stable pharmaceutical composition. Studies have found that due to the unique property of compound A itself, conventional compositions are difficult to be stored stably. When conventional compositions are placed under accelerated conditions, there is a significant increase in related substances. Therefore, it is necessary to provide a stable pharmaceutical composition comprising compound A.

SUMMARY OF THE INVENTION

The object of the present invention is to provide a rapidly dissolving pharmaceutical composition, which has good stability.

The pharmaceutical composition according to the present invention comprises (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide or a salt thereof, and a cellulose ether. The cellulose ether used in the present invention can be selected from the group consisting of alkyl cellulose, hydroxyalkyl cellulose and hydroxyalkyl alkyl cellulose. The alkyl cellulose can be selected from the group consisting of methyl cellulose, ethyl cellulose, etc.; the hydroxyalkyl cellulose can be selected from the group consisting of hydroxyethyl cellulose, hydroxypropyl cellulose, etc.; and the hydroxyalkyl alkyl cellulose can be selected from the group consisting of hydroxyethyl methyl cellulose and hydroxypropyl methyl cellulose. In a preferred embodiment, the cellulose ether is hydroxypropyl methyl cellulose, more preferably hydroxypropyl methyl cellulose E5.

Due to the addition of the above cellulose ether, the stability of the active ingredient is ensured. The present invention has surprisingly found that when a conventional binder in the art (such as polyvinylpyrrolidone and starch) is used, the active ingredient in the present invention degrades rapidly, while the composition added with cellulose ether remains stable. The pharmaceutical composition of the present invention is placed under an open condition at a temperature of 40° C. and relative humidity of 75% for 7 days, and then the degradation products are determined by HPLC. The increase of the degradation products do not exceed 0.5%, preferably 0.4%, more preferably 0.3%, further preferably 0.2%, and most preferably 0.1%.

The above stabilizing effect can be achieved merely by a small amount of the cellulose ether of the present invention. In a preferred embodiment, the cellulose ether is present in an amount of 0.5-15%, preferably 1-10%, more preferably 1.5-5%, and most preferably 2-3% by weight, relative to the total weight of the composition.

The active ingredient of the present invention can be present in an amount of 0.1%-30%, preferably 0.5%-20% by weight, relative to the total weight of the composition. In a specific unit dose composition, the active ingredient is present in an amount of 0.35 mg to 70 mg, preferably 0.5-60 mg.

When the active ingredient of the present invention is present in the form of a pharmaceutically acceptable salt, the salt can be an acid addition salt formed from (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide and various organic or inorganic acids, preferably a bisulfate.

The pharmaceutical composition according to the present invention can further comprise one or more of a filler, a disintegrant, and a lubricant.

The filler in the composition of the present invention can comprise, but is not limited to, one or more of lactose, microcrystalline cellulose, mannitol, and pregelatinized starch. The filler can be present in an amount of 20%-95%, preferably 40%-95%, and more preferably 50%-90% by weight, relative to the total weight of the composition.

The disintegrant can comprise, but is not limited to, one or more of croscarmellose sodium, sodium carboxymethyl starch and crospovidone. The disintegrant can be present in an amount of 1%-20% by weight, relative to the total weight of the composition.

The lubricant can comprise, but is not limited to, one or more of talc, magnesium stearate, zinc stearate, glyceryl behenate, sodium lauryl sulfate, hydrogenated vegetable oil, and colloidal silicon dioxide. The lubricant can be present in an amount of 0.5%-5% by weight, relative to the total weight of the composition.

In a particularly preferred embodiment of the present invention, the pharmaceutical composition of the present invention comprises the following ingredients:

1) 0.1%-30% by weight of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide or a pharmaceutically acceptable salt thereof;
2) 1-10% by weight of hydroxypropyl methyl cellulose;
3) 40%-95% by weight of a filler, wherein the filler comprises lactose and microcrystalline cellulose;
4) 1%-20% by weight of a disintegrant, wherein the disintegrant is one or both of croscarmellose sodium and carboxymethyl starch sodium;
5) optionally 0.5%-5% by weight of magnesium stearate.

The dissolution test is carried out on the pharmaceutical composition of the present invention according to the second method (paddle method) of the dissolution rate test described in the appendix of volume II of Chinese Pharmacopoeia 2010 Edition, using a 0.1 mol/L hydrochloric acid solution as a dissolution medium at 37±0.5° C. and at a paddle speed of 50 rpm. With respect to the unit dose of the pharmaceutical composition of the present invention, the dissolution medium is preferably 1000 ml. It is determined by the test that the dissolution rate of the bisulfate of (3aR,5s,6aS)-N-(3-methoxy-1,2,4-thiadiazol-5-yl-5-(methyl(7H-pyrrolo[2,3-d]pyrimidine-4-yl)amino)hexahydrocyclopenta[c]pyrrol-2(1H)-carboxamide is greater than 92%, preferably greater than 93%, more preferably greater than 94%, and most preferably greater than 95% in 60 minutes; more preferably, the dissolution rate of the active ingredient in the composition is greater than 95% in 45 minutes.

The pharmaceutical composition of the present invention can be prepared by a method commonly used in the art, which comprises mixing the bisulfate of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide with at least one cellulose ether and at least one pharmaceutically acceptable excipient, and granulating the mixture. The granules of the pharmaceutical composition are prepared by a granulation method, for example high shear wet granulation or one step granulation. The granules can then be prepared into oral solid formulations such as tablets or capsules etc.

The pharmaceutical composition of the present invention improves the stability of the active ingredient, and has an excellent dissolution effect. The preparation method is simple and suitable for industrial production.

DETAILED DESCRIPTION OF THE INVENTION

Figure 1:
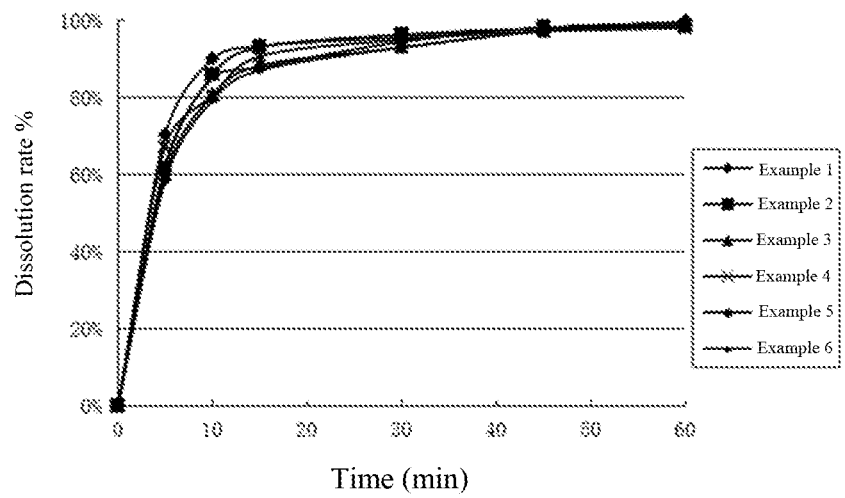
FIG. 1 shows the dissolution profiles of the tablets of Examples 1 to 6 in a 0.1 mol/L hydrochloric acid solution.

The present invention is further described in detail by the following examples and experimental examples. These examples and experimental examples are for illustrative purposes only, and are not intended to limit the scope of the present invention.

In the following examples, compound A is used to represent the bisulfate of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2 (1H)-carboxamide.

Examples 1 to 6

Compound A, mannitol, lactose, microcrystalline cellulose, pregelatinized starch, and croscarmellose sodium were mixed well according to the ratio shown in Table 1. Wet granulation was carried out using a 4% aqueous solution of hydroxypropyl methyl cellulose E5 as a wetting agent. The granules were compressed into tablets.

TABLE 1

| Ingredients | Example 1 | Example 2 | Example 3 | Example 4 | Example 5 | Example 6 |
|---|---|---|---|---|---|---|
| Compound A | 0.5 | 15 | 35 | 65 | 50 | 50 |
| Mannitol | — | — | — | — | 274.3 | 274.1 |
| Lactose | 56.20 | 101.1 | 85.3 | 256.8 | — | — |
| Pregelatinized starch | — | — | — | — | — | 77.55 |
| Microcrystalline cellulose | 27.0 | 50.6 | 42.6 | 129.0 | 137.2 | 137.0 |
| CCNa | 3.6 | 7.2 | 10.8 | 30.0 | 20.0 | 20.0 |
| HPMC E5 | 1.8 | 4.3 | 4.5 | 14.2 | 13.5 | 13.9 |
| Purified water | 43.2 | 103.2 | 108.0 | 340.8 | 324.0 | 333.6 |
| Magnesium stearate | 0.9 | 1.8 | 1.8 | 5.0 | 5.0 | 5.0 |
| Total | 90 | 180 | 180 | 500 | 500 | 500 |

Unit: mg

Examples 7 to 9

Compound A, lactose, microcrystalline cellulose, sodium carboxymethyl starch, and crospovidone were mixed well according to the ratio shown in Table 2. Wet granulation was carried out using a 4% aqueous solution of hydroxypropyl methyl cellulose E15 as a wetting agent. The granules were compressed into tablets.

TABLE 2

| Ingredients | Example 7 | Example 8 | Example 9 |
|---|---|---|---|
| Compound A | 12 | 20 | 20 |
| Lactose | 104.2 | 95.4 | 85.3 |
| Microcrystalline cellulose | 50.6 | 47.7 | 42.6 |
| CMS-Na | 7.2 | 10.8 | — |
| PVPP | — | — | 14.4 |
| HPMC E15 | 4.2 | 4.3 | 4.5 |
| Purified water | 100.8 | 103.2 | 108.0 |
| Magnesium stearate | 1.8 | 1.8 | 1.8 |
| Total | 180 | 180 | 180 |

Unit: mg

Examples 10 to 12

Compound A, lactose, microcrystalline cellulose, and croscarmellose sodium were mixed well according to the prescription ratio shown in Table 3. Wet granulation was carried out using a 10% aqueous solution of polyvinylpyrrolidone, a 10% aqueous solution of starch, and a 4% aqueous solution of hydroxypropyl methyl cellulose as a wetting agent, respectively. The granules were compressed into tablets of Examples 10 to 12.

TABLE 3

| Ingredients | Example 10 | Example 11 | Example 12 |
|---|---|---|---|
| Compound A | 20 | 20 | 20 |
| Lactose | 91.86 | 92.19 | 95.9 |
| Microcrystalline cellulose | 46.0 | 46.0 | 48.0 |
| Croscarmellose sodium | 7.2 | 7.2 | 7.2 |
| PVP K30 | 9.54 | — | — |
| Starch | — | 9.21 | — |
| HPMC E5 | — | — | 4.6 |
| Purified water | 85.86 | 82.89 | 110.4 |
| Magnesium stearate | 1.8 | 1.8 | 1.8 |
| Total | 180 | 180 | 180 |

Unit: mg

Example 13

Preparation of Compound A 1.0 g (2.4 mmol) of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide was added to a 50 ml Erlenmeyer flask, followed by addition of 12 ml of dichloromethane and 3 ml of anhydrous methanol. The mixture was stirred at room temperature, and then 0.25 g (2.5 mmol) of concentrated sulfuric acid was added dropwise. After the suspension became clear, the insoluble substances were removed by filtration. No solid was precipitated after the filtrate was stirred for 6 hours. Then, 10 ml of isopropanol was added, and then a large amount of white solid was precipitated. The mixture was stirred for another 18 hours, filtered and dried to obtain 1.138 g of a white solid in a yield of 92.1%.

Experimental Example 1

Dissolution Test

Figure 2:
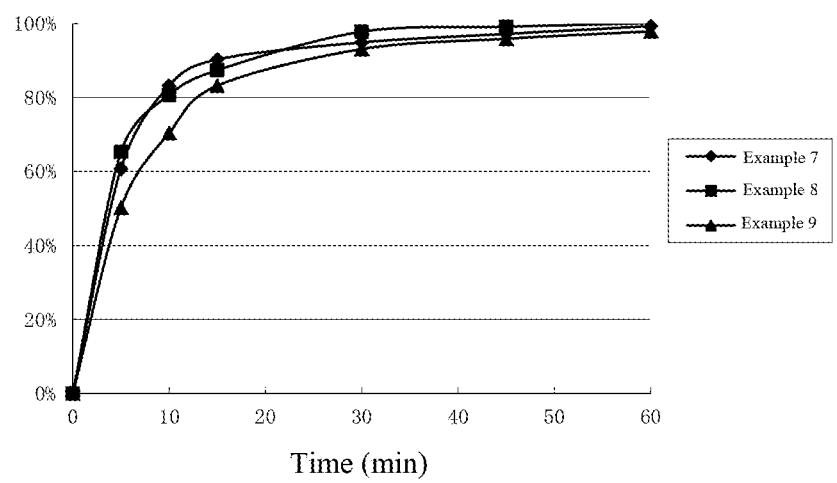
FIG. 2 shows the dissolution profiles of the tablets of Examples 7 to 9 in a 0.1 mol/L hydrochloric acid solution.
Figure 3:
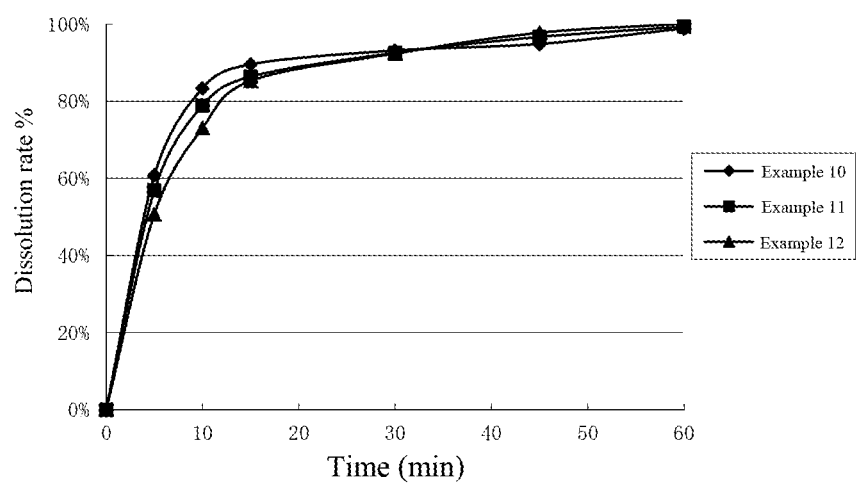
FIG. 3 shows the dissolution profiles of the tablets of Examples 10 to 12 in a 0.1 mol/L hydrochloric acid solution.

The dissolution rates of the tablets of Examples 1-12 were determined according to the second method (paddle method) of the dissolution rate test described in the appendix of volume II of Chinese Pharmacopoeia 2010 Edition. The dissolution test was carried out using 1000 ml of 0.1 mol/L hydrochloric acid solution as a dissolution medium at 37±0.5° C. and at a paddle speed of 50 rpm. The dissolution profiles are shown in FIGS. 1, 2 and 3. The results of dissolution rates are shown in Table 4, 5 and 6.

TABLE 4

Results of dissolution rates of various formulations in Examples 1-6

| | Dissolution rate (%) | | | | | |
|---|---|---|---|---|---|---|
| Time (min) | Example 1 | Example 2 | Example 3 | Example 4 | Example 5 | Example 6 |
| 5 | 70.4% | 61.7% | 60.1% | 67.4% | 58.6% | 62.7% |
| 10 | 90.1% | 85.9% | 80.7% | 80.4% | 79.4% | 85.1% |
| 15 | 93.5% | 93.2% | 88.4% | 90.8% | 87.2% | 87.9% |
| 30 | 95.7% | 96.4% | 93.1% | 95.1% | 93.1% | 94.6% |
| 45 | 98.2% | 98.1% | 97.4% | 97.3% | 97.4% | 98.2% |
| 60 | 99.7% | 98.6% | 98.8% | 98.1% | 99.6% | 99.5% |

In Examples 1-6, the tablets dissolve rapidly and completely; in Examples 4-5, although the content of API is high, the prepared tablets can still dissolve rapidly and completely.

TABLE 5

Results of dissolution rates of various formulations in Examples 7-9

| | Dissolution rate (%) | | |
|---|---|---|---|
| Time (min) | Example 7 | Example 8 | Example 9 |
| 5 | 60.7% | 65.3% | 50.2% |
| 10 | 83.2% | 80.7% | 70.4% |
| 15 | 90.3% | 87.4% | 83.2% |
| 30 | 94.9% | 97.8% | 93.1% |
| 45 | 97.2% | 99.1% | 95.9% |
| 60 | 99.3% | 100.1% | 97.9% |

TABLE 6

Results of dissolution rates of various formulations in Examples 10-12

| | Dissolution rate (%) | | |
|---|---|---|---|
| Time (min) | Example 10 | Example 11 | Example 12 |
| 5 | 60.8% | 56.9% | 50.7% |
| 10 | 83.4% | 78.9% | 73.1% |
| 15 | 89.6% | 86.4% | 85.3% |
| 30 | 93.2% | 92.6% | 92.4% |
| 45 | 94.9% | 96.7% | 97.8% |
| 60 | 98.9% | 99.4% | 100.1% |

The results of Examples 7-12 show that the prepared tablets can dissolve rapidly and completely.

Experimental Example 2

Stability Test

The tablets of Examples 9, 10, 11 and 12 were placed under an open condition at a temperature of 40° C. and relative humidity of 75% for 7 days, and then the degradation products were determined by a HPLC method.

The results of degradation products test show that, with respect to the tablets of Examples 9 and 12 in which hydroxypropyl methyl cellulose was used as the binder, the degradation products did not increase. However, with respect to the tablets of Examples 10 and 11 in which polyvinylpyrrolidone and starch were used as the binder respectively, the degradation products increased obviously (see Table 7).

TABLE 7

|  | Initial state | | Placed for 7 days | |
| --- | --- | --- | --- | --- |
|  | Degradation products (%) | Content of compound A (%) | Degradation products (%) | Content of compound A (%) |
| Example 9 | 0.82 | 99.46 | 0.84 | 99.56 |
| Example 10 | 0.84 | 99.67 | 1.34 | 99.73 |
| Example 11 | 0.79 | 99.84 | 1.42 | 99.89 |
| Example 12 | 0.86 | 100.12 | 0.84 | 100.01 |

What is claimed is:

1. A pharmaceutical composition, comprising (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide or a pharmaceutically acceptable salt thereof, and hydroxypropyl methyl cellulose in an amount of 1-10% by weight, relative to the total weight of the pharmaceutical composition.

2. The pharmaceutical composition according to claim 1, further comprising a filler, wherein the filler comprises one or more selected from the group consisting of lactose, microcrystalline cellulose, mannitol, and pregelatinized starch.

3. The pharmaceutical composition according to claim 1, further comprising a disintegrant, wherein the disintegrant comprises one or more selected from the group consisting of croscarmellose sodium, sodium carboxymethyl starch and crospovidone.

4. The pharmaceutical composition according to claim 1, further comprising a lubricant, wherein the lubricant comprises one or more selected from the group consisting of talc, magnesium stearate, zinc stearate, glyceryl behenate, sodium lauryl sulfate, hydrogenated vegetable oil, and colloidal silicon dioxide.

5. A pharmaceutical composition, comprising:
1) 0.1%-30% by weight of (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide or a pharmaceutically acceptable salt thereof;
2) 1-10% by weight of hydroxypropyl methyl cellulose;
3) 40%-95% by weight of a filler, wherein the filler comprises lactose and microcrystalline cellulose;
4) 1%-20% by weight of a disintegrant, wherein the disintegrant is one or both of croscarmellose sodium and carboxymethyl starch sodium; and
5) optionally 0.5%-5% by weight of magnesium stearate.

6. A method for preparing the pharmaceutical composition according to claim 1, comprising mixing (3aR,5s,6aS)-N-(3-methoxy-1,2,4-thiadiazol-5-yl)-5-(methyl(7H-pyrrolo[2,3-d]pyrimidine-4-yl)amino)hexahydrocyclopenta[c]pyrrol-2(1H)-carboxamide or a pharmaceutically acceptable salt thereof with the hydroxypropyl methyl cellulose to obtain a mixture, and granulating the mixture.

7. A method for treating a disease associated with JAK kinase in a subject in need thereof, comprising administering to the subject the pharmaceutical composition of claim 1.

8. The method according to claim 7, wherein the disease is selected from the group consisting of rheumatic and rheumatoid arthritis.

9. A method for treating a disease associate with JAK kinase in a subject in need thereof, comprising administering to the subject the pharmaceutical composition of claim 5.

10. The method according to claim 9, wherein the disease is selected from the group consisting of rheumatic and rheumatoid arthritis.

11. The pharmaceutical composition according to claim 1, wherein the hydroxypropyl methyl cellulose is present in an amount 1.5-5% by weight, relative to the total weight of the pharmaceutical composition.

12. The pharmaceutical composition according to claim 1, wherein the hydroxypropyl methyl cellulose is present in an amount 2-3% by weight, relative to the total weight of the pharmaceutical composition.

* * * * *